(12) United States Patent
Chen et al.

(10) Patent No.: US 11,850,015 B2
(45) Date of Patent: Dec. 26, 2023

(54) MANIPULATOR DRIVEN BY MODULAR JOINT TIME-SHARING SWITCHING

(71) Applicant: ZHEJIANG UNIVERSITY, Zhejiang (CN)

(72) Inventors: Jian Chen, Hangzhou (CN); Luhang Cui, Hangzhou (CN); Keji Yang, Hangzhou (CN); Yunjiang Wang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 18/097,506

(22) Filed: Jan. 17, 2023

(65) Prior Publication Data
US 2023/0181273 A1    Jun. 15, 2023

Related U.S. Application Data

(63) Continuation of application No. PCT/CN2021/106632, filed on Jul. 16, 2021.

(30) Foreign Application Priority Data

Apr. 22, 2021  (CN) .......................... 202110438246.7

(51) Int. Cl.
 *A61B 34/00* (2016.01)
 *A61B 34/30* (2016.01)
 *A61B 17/00* (2006.01)

(52) U.S. Cl.
 CPC .............. *A61B 34/70* (2016.02); *A61B 34/30* (2016.02); *A61B 2017/00867* (2013.01)

(58) Field of Classification Search
 CPC ........... A61B 2017/00309; A61B 2017/00323; A61B 2017/00867; A61B 34/30; A61B 34/70; A61B 34/71
 See application file for complete search history.

(56) References Cited

U.S. PATENT DOCUMENTS 6,306,141 B1 * 10/2001 Jervis ...................... A61F 6/14
 606/78
2004/0138700 A1   7/2004 Cooper et al.
(Continued)

FOREIGN PATENT DOCUMENTS

CN   102873690 A   1/2013
CN   106073833 A   11/2016
(Continued)

OTHER PUBLICATIONS

International Search Report (PCT/CN2021/106632); dated Jan. 19, 2022.
CN First Office Action(202110438246.7 ); dated Apr. 2, 2022.

*Primary Examiner* — Scott Luan
(74) *Attorney, Agent, or Firm* — W&G Law Group

(57) ABSTRACT

A dexterous operation arm driven by modular joint time-sharing switching, the operation arm comprising a plurality of completely identical sub-sections, each sub-section comprising three parts: an external elbow assembly, an internal transmission assembly, and an elbow drive unit. The tail end of the operation arm can be connected to end effectors, such as claws, tweezers, scissors, and the like, to form a dexterous micro-device, which is mounted at the tail end of a minimally invasive surgical robotic system to assist in minimally invasive surgery. The operation arm modularizes operation arm joints, and separates the drive of each joint, which improves the flexibility of the operation arm, and can enable dexterously delivering an end effector to the vicinity of a lesion for surgery.

5 Claims, 4 Drawing Sheets

(56) References Cited

U.S. PATENT DOCUMENTS

2012/0123395 A1   5/2012  Stoy et al.
2013/0213170 A1   8/2013  Kim et al.
2018/0214144 A1   8/2018  Fischvogt et al.

FOREIGN PATENT DOCUMENTS

| CN | 106175850 A | 12/2016 |
|----|-------------|---------|
| CN | 106714655 A | 5/2017  |
| CN | 109700537 A | 5/2019  |
| CN | 110788846 A | 2/2020  |
| CN | 110811840 A | 2/2020  |
| CN | 112405606 A | 2/2021  |
| EP | 3682835 A1  | 7/2020  |

\* cited by examiner

MANIPULATOR DRIVEN BY MODULAR JOINT TIME-SHARING SWITCHING

CROSS-REFERENCE TO RELATED APPLICATIONS

The present application is a National Phase of International Application No. PCT/CN2021/106632, filed on Jul. 16, 2021, which claims priority to Chinese Application No. 202110438246.7, filed on Apr. 22, 2021, the contents of both of which are incorporated herein by reference in their entireties.

TECHNICAL FIELD

The present disclosure relates to the field of medical apparatus, especially a micro apparatus in a minimally invasive surgery robot system, and in particular, to a multi-degree-of-freedom manipulator for minimally invasive surgery.

BACKGROUND

At present, minimally invasive surgery has been popular and recognized as the mainstream scheme for many surgeries, and increasingly relies on micro apparatuses that are conducive to dexterous operation to implement ultimate surgical operations. The surgical robot system, represented by da Vinci system, has been widely adopted in minimally invasive surgery. The surgical robot system uses a single or multiple millimeter sized traumas on the body surface to establish a surgical channel, and a micro apparatus composed of an end executor and a manipulator enters the surgical site through the channel. The minimally invasive surgery can result in such a small trauma that the size of the micro apparatus at the end of the surgical robot system is required to be small enough, and the motion space and dexterously multi-degree-of-freedom operation are required at the same time.

At present, due to the limited space, the motors are rear-positioned in the micro apparatuses at the end of most robot systems and each degree-of-freedom motion is pulled by means of rope-transmission movement. Multi-degree-of-freedom movement requires a dexterous transmission arrangement, and the limited space needs to be skillfully used to arrange a dexterous transmission structure, which bring the following problems: i) multiple degrees of freedom need to be driven separately by ropes, which leads to an increase in the number of ropes and difficulty in wiring; ii) serious couplings among each degree of freedom lead to complex control and low transmission accuracy; iii) the number of degrees of freedom relies significantly on the space required by the transmission mechanism, which limits the degree of freedom of the entire manipulator.

SUMMARY

In order to meet the requirements of minimally invasive surgery on the size and flexibility of apparatuses, solve the problem of transmission difficulty, and enable the manipulator to reach the vicinity of a lesion dexterously or free surgery without losing the degree of freedom of the end executor, the present disclosure provides a dexterous and flexible manipulator driven by modular joint time-sharing switching to improve the dexterity of surgical operations performed by the minimally invasive surgical robots.

The technical solution adopted by the present disclosure in view of the deficiencies of the related art is as follows: a dexterous and flexible manipulator driven by modular joint time-sharing switching, including N identical sub segments, each of which includes three parts: an external elbow tube assembly, an internal transmission assembly and an elbow tube drive unit.

The external elbow tube assembly includes a fixed outer tube, an outer tube connecting sleeve I, a flexible outer tube, a driving nickel titanium wire, a supporting nickel titanium wire and a second outer tube connecting sleeve.

The fixed outer tube is a non-bendable sleeve structure, and is provided with a sliding groove symmetrical at both sides of a tube wall of the fixed outer tube. One end of the sliding groove extends to the end face of the fixed outer tube. The first outer tube connecting sleeve is a sleeve structure, one end of which is provided with a shaft shoulder to connect with the fixed outer tube, and the other end of which is connected with the flexible outer tube. The flexible outer tube is a unidirectional and bendable sleeve structure, both ends of which are connected with the first outer tube connecting sleeve and the previous segment of the second outer tube connecting sleeve, respectively, through shaft shoulders at both ends of the flexible outer tube. The tube wall of the flexible outer tube is provided with through holes evenly arranged along a circumference. The through holes are divided into four groups at the upper, lower, left and right sides, respectively. The groups of through holes at the left and right sides are configured for mounting the supporting nickel titanium wire, and one of the groups of through holes at the upper and lower sides are configured for mounting the driving nickel titanium wire. The supporting nickel titanium wire and the driving nickel titanium wire are both made of hyperelastic nickel titanium alloy wires. The second outer tube connecting sleeve is a sleeve structure with an inner shaft shoulder, both ends of which are connected with the fixed outer tube and a next segment of the flexible outer tube, respectively.

The internal transmission assembly includes a transmission shaft core, an inner tube connecting sleeve and a flexible inner tube.

The transmission shaft core is a hollow shaft structure, both ends of which are connected with the inner tube connecting sleeve through internal splines, respectively. The inner tube connecting sleeve is a sleeve structure, one end of which is connected with the transmission shaft core with an external spline, and the other end of which is connected with the flexible inner tube. The flexible inner tube is a flexible hollow shaft structure, both ends of which are connected with the inner tube connecting sleeve through a shaft-milling plane structure.

The elbow tube drive unit includes a threaded tube, a flange block, a threaded collar, an annular slide block and a temperature-controlled nickel titanium wire.

The threaded tube is a sleeve structure with smooth inner wall, and is provided with a threaded structure at an outer side of the threaded tube. The threaded tube and the flange block are sleeved sequentially on the transmission shaft core. The threaded collar is sleeved outside the threaded tube to form thread transmission. The inner side of the annular slide block and the treaded collar are fitted with each other to fix the driving nickel titanium wire. The ear of the annular slide block is a bump structure, which is slidable along the axial direction of the fixed outer tube in the sliding grooves of the fixed outer tube.

Further, the flexible outer tube is a bendable but non-torsional nickel titanium alloy tube, and is provided with opposite spaced notches at both sides of the flexible outer tube to improve the bending performance of the flexible outer tube.

Further, the both ends of the supporting nickel titanium wire are clamped at the flexible outer tube by the first outer tube connecting sleeve and the previous segment of the second outer tube connecting sleeve, respectively, to improve the torsional resistance of the corrugated flexible outer tube.

Further, one end of the driving nickel titanium wire is clamped at the flexible outer tube by the second outer tube connecting sleeve, and the other end is clamped between the threaded collar and the annular slide block. The threaded collar and the annular slide block manipulate the nickel titanium wire to achieve the bending of the flexible outer tube.

Further, a plurality of wiring channels are arranged in the tube wall of the transmission shaft core for arranging electric wires and the temperature-controlled nickel titanium wire.

Further, the transmission shaft core is provided with a step which is capable of achieving a micro-displacement along the axial direction of the transmission shaft core. The step is provided with two pinholes. The temperature-controlled nickel titanium wire is led out of the tube wall of the transmission shaft core and returns to the tube wall of the transmission shaft core after passing through the pinholes.

Further, the flexible inner tube is a bendable but non-torsional nickel titanium alloy tube provided with opposite spaced notches at both sides of the flexible inner tube to improve the bending performance of the flexible inner tube.

Further, the flange block is fixedly sleeved on the transmission shaft core, and the transmission shaft core is provided with two pinholes at the matching position with the flange block leading out the temperature-controlled nickel titanium wire from the tube wall of the transmission shaft core. The flange block and the transmission shaft core are connected with each other to fix both ends of the temperature-controlled nickel titanium wire.

Further, the temperature-controlled nickel titanium wire is an energized-contractive nickel titanium alloy wire, which is capable of driving the step on the transmission shaft core to implementing a micro-displacement along the axial direction of the transmission shaft, so that the transmission shaft core contacts with the threaded tube and drives the threaded tube to rotate through friction.

The beneficial effect of the present disclosure is that the manipulator proposed by the present disclosure includes modular joints, and the driving of each joint is independent of each other. The elbow tube drive unit of each joint is connected with the internal transmission assembly by time-sharing switching, which can achieve the independent bending of each joint. Since the bending force of each joint comes from the rotation of the internal transmission assembly, without providing a solo power supply and a transmission component separately for each degree of freedom, so the transmission wiring is simple. Since the bending of each joint is time-sharing independent, there is no coupling among each degree of freedom of each joint, which results in simple control and high transmission accuracy. Since the bending of each joint is carried out by connecting the elbow tube drive unit with the internal transmission assembly by time-sharing switching, the degree of freedom of the entire manipulator is capable of being flexibly increased or decreased by the number of the joint modules. Due to the skillfully designed transmission structure of the manipulator, the present disclosure meets the requirements of minimally invasive surgery on the size and dexterity of the manipulator. By connecting the end of the manipulator to end executors such as claw forceps, tweezers and scissors, the end executors can be accurately sent to the working area and assist surgeons to complete minimally invasive surgery.

Figure 1:
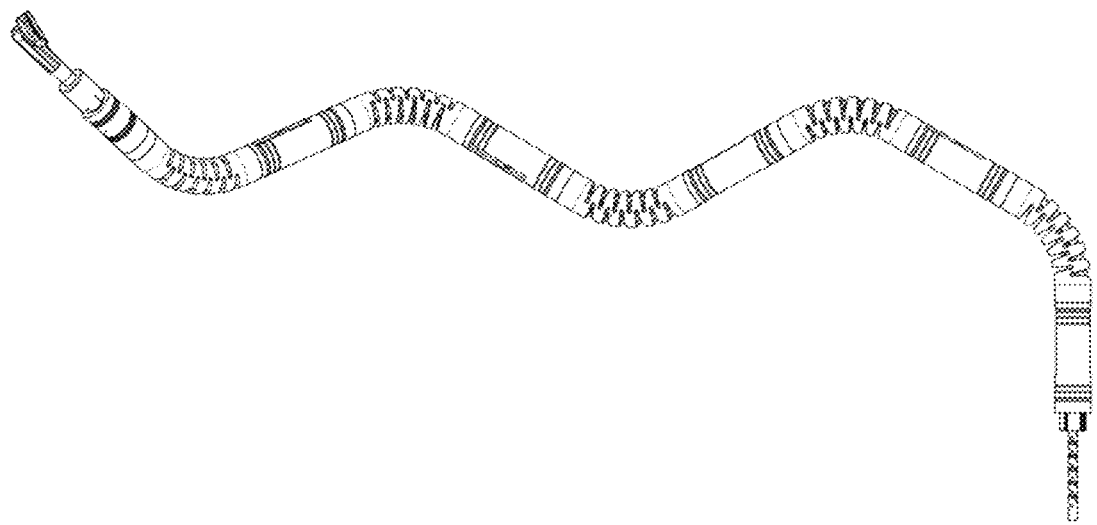
FIG. 1 is an appearance effect diagram.

Reference signs: 1—flexible outer tube, 2—first outer tube connecting sleeve, 3—threaded collar, 4—annular slide block, 5—fixed outer tube, 6—second outer tube connecting sleeve, 7—inner tube connecting sleeve, 8—transmission shaft core, 9—threaded tube, 10—flange block, 11—flexible inner tube, 12—supporting nickel titanium wire, 13—driving nickel titanium wire, 14—temperature-controlled nickel titanium wire.

DESCRIPTION OF EMBODIMENTS

The present disclosure will be further described in detail below in combination with the drawings and specific embodiments.

As shown in FIGS. 1-5, the present disclosure provides a dexterous manipulator driven by modular joint time-sharing switching, including N identical sub segments, each of which includes three parts: an external elbow tube assembly, an internal transmission assembly, and an elbow tube drive unit.

The external elbow tube assembly includes a fixed outer tube 5, a first outer tube connecting sleeve 6, a flexible outer tube 1, a driving nickel titanium wire 13, a supporting nickel titanium wire 12 and a second outer tube connecting sleeve 6.

The fixed outer tube 5 is a non-bendable sleeve structure, and is provided with sliding groove symmetrical at both sides of a tube wall of the fixed outer tube 5. One end of the sliding groove extends to the end face of the fixed outer tube 5. The first outer tube connecting sleeve 6 is a sleeve structure, one end of which is provided with a shaft shoulder to connect with the fixed outer tube 5, and the other end of which is connected with the flexible outer tube 1. The flexible outer tube 1 is a unidirectional and bendable sleeve structure, the both ends of which are connected with the first outer tube connecting sleeve 6 and the previous segment of the second outer tube connecting sleeve 6, respectively, through shaft shoulders provided at both ends of the flexible outer tube 1. The tube wall of the flexible outer tube 1 is provided with through holes evenly arranged along the circumference. The through holes are divided into four groups at the upper, lower, left and right sides, respectively. The groups of through holes at the left and right sides are configured for mounting the supporting nickel titanium wire 12, and one of the groups of through holes at the upper and lower sides is configured for mounting the driving nickel titanium wire 13. The supporting nickel titanium wire 12 and the driving nickel titanium wire 13 are both made of hyperelastic nickel titanium alloy wires. The second outer tube connecting sleeve 6 is a sleeve structure with an internal shaft shoulder, both ends of which are connected with the fixed outer tube 5 and the next segment of the flexible outer tube 1, respectively, through shaft shoulders provided at both ends of the flexible outer tube 1.

The internal transmission assembly includes a transmission shaft core 8, an inner tube connecting sleeve 7 and a flexible inner tube 11.

The transmission shaft core 8 is a hollow shaft structure, and is provided with internal splines at both ends of the transmission shaft core 8, which are connected with the inner tube connecting sleeve 7, respectively. The inner tube connecting sleeve 7 is a sleeve structure, one end of which is provided with an external spline to connect with the transmission shaft core 8, and the other end of which is connected with the flexible inner tube 11. The flexible inner tube 11 is a flexible hollow shaft structure, both ends of which are connected with the inner tube connecting sleeve 7 through a shaft-milling plane structure.

The elbow tube drive unit includes a threaded tube 9, a flange block 10, a threaded collar 3, an annular slide block 4 and a temperature-controlled nickel titanium wire 14.

The threaded tube 9 is a sleeve structure with smooth inner wall, and is provided with a threaded structure at the outer side of the threaded tube 9. The threaded tube 9 and the flange block 10 are sleeved sequentially on the transmission shaft core 8. The threaded collar 3 is sleeved outside the threaded tube 9 to form thread transmission. The inner side of the annular slide block 4 and the threaded collar 3 can be fitted with each other to fix the driving nickel titanium wire 13. The ear of the annular slide block 4 is a bump structure, which can slide along the axial direction of the fixed outer tube 5 in the sliding grooves of the fixed outer tube 5.

Embodiment 1

A micro apparatus was mounted on a minimally invasive surgical robot system by connecting the end of the manipulator to end executors such as claw forceps, tweezers and scissors, which can accurately send the end executors to the working area and assist the surgeon to complete the surgery.

Figure 4:
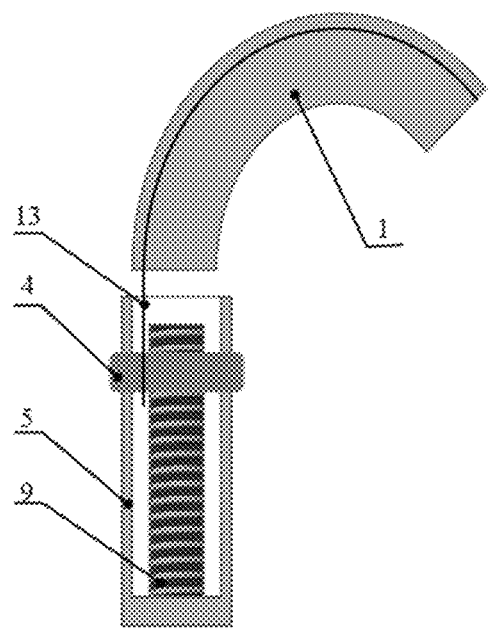
FIG. 4 is a bending schematic diagram of a flexible outer tube.
Figure 5:
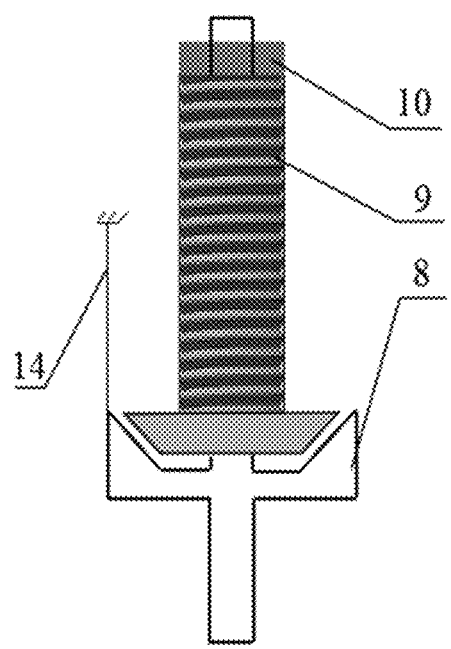
FIG. 5 is a working schematic diagram of a drive unit.
Figure 6:
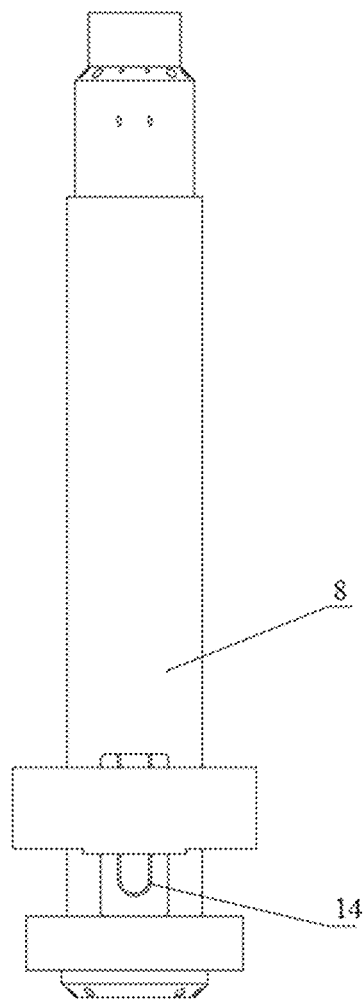
FIG. 6 is a connecting relationship diagram of some parts.

As shown in FIG. 1, the entire manipulator was composed of N identical sub segments, and the bending of the entire manipulator was composed of the bending of the flexible outer tube 1 of each sub segment. The internal transmission assembly of the surgical robot system was driven by a motor to rotate. Since the sub segments were connected together through the inner tube connecting sleeve 7, the internal transmission assembly of all segments were rotatable. The time-sharing switching drive of each sub segment was mainly controlled by the temperature-controlled nickel titanium wire 14 of each segment. The temperature-controlled nickel titanium wire 14 was connected to a control circuit through the lines in the shaft wall of the transmission shaft core 8, and the bending of the segment was achieved by controlling the energized contraction of the temperature-controlled nickel titanium wire 14 of different segments. In an embodiment, the energized contraction of the temperature-controlled nickel titanium wire 14 would drive the threaded tube 9 to rotate, and the rotation of the threaded tube 9 would drive the flexible outer tube 1 to bend. As shown in FIGS. 5 and 6, the implementation process of the rotation of the threaded tube 9 is as follows: the temperature-controlled nickel titanium wire 14 was controlled to be energized-contracted to pull the step of the transmission shaft core 8 to generate deformation, so as to achieve the contact between the threaded tube 9 and the transmission shaft core 8. The transmission shaft core 8 transmitted the rotation to the threaded tube 9 through friction. When the temperature-controlled nickel titanium wire 14 was powered off, the step of the transmission shaft core 8 would disconnect the contact with the threaded tube 9 under the elasticity effect thereof, and the rotation of the threaded tube 9 would stop. As shown in FIG. 4, the bending process of the flexible outer tube 1 is as follows: the threaded tube 9 rotated and driven the threaded collar 3 and the annular slide block 4 to slide in the sliding grooves of the fixed outer tube 5 through a thread pair, thus the driving nickel titanium wire 13 was driven to move, and the flexible outer tube 1 war driven by the nickel titanium wire 13 to bend.

Embodiment 2

As shown in FIG. 1, the entire manipulator was composed of N identical sub segments. The end of the manipulator was capable of being connected with simple end executors such as claw forceps, tweezers and scissors. Since the transmission shaft core 8 was the hollow shaft structure, the actions of the end executors were capable of being transmitted through the internal channel of the transmission shaft core 8. By reasonably controlling the temperature-controlled nickel titanium wire 14 of each sub segment, the robot system was capable of flexibly changing the position and posture of the manipulator. In particular, when it was unavoidable to bypass some crucial human tissues, the manipulator according to the present disclosure was capable of sending end executors to the vicinity of a lesion more flexibly and freely, and assisting in completing some minimally invasive surgical operations, such as ultrasonic ablation, tissue removal, suture and drug injection.

Embodiment 3

Figure 2:
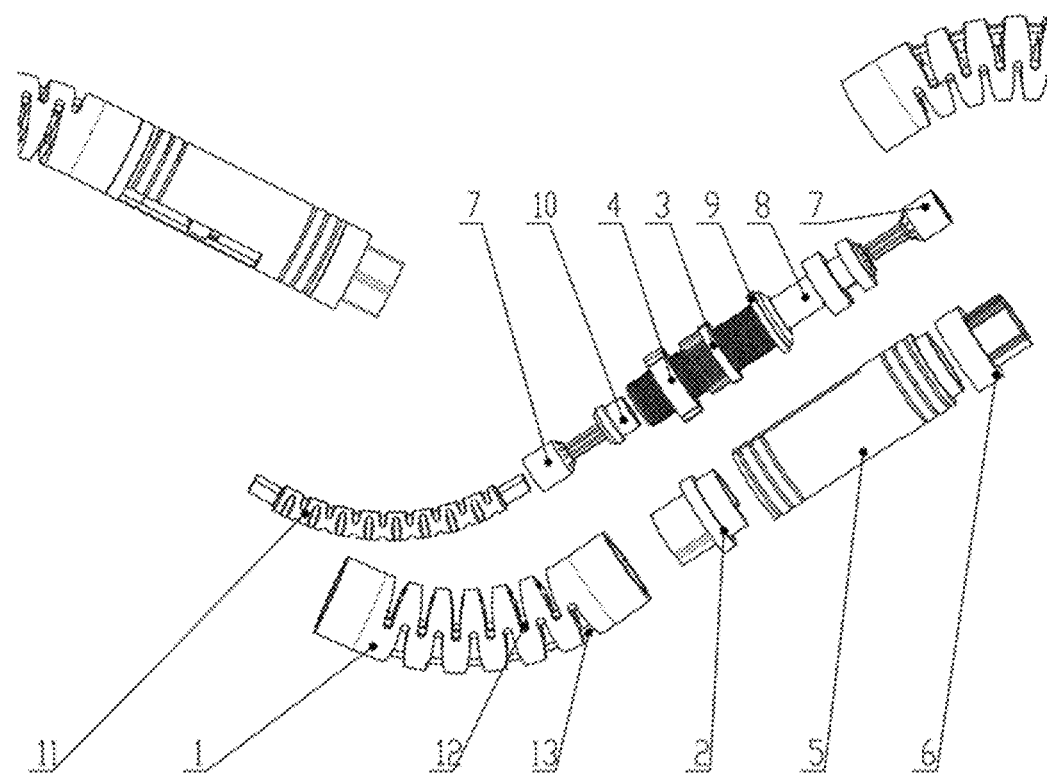
FIG. 2 is an exploded diagram of a sub segment.
Figure 3:
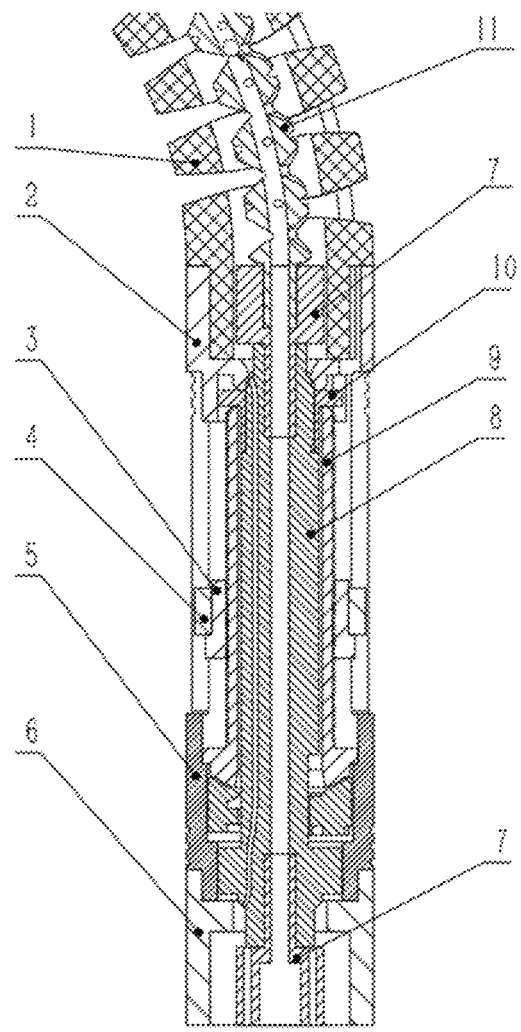
FIG. 3 is a partial sectional diagram.

As shown in FIG. 2, each sub segment included three parts: the external elbow tube assembly, the internal transmission assembly and the elbow tube drive unit. The function and structure of each sub segment are the same. Therefore, by increasing the number of sub segments and the connecting the second outer tube connecting sleeve 6 and the inner tube connecting sleeve 7, the degree of freedom of the entire manipulator would be increased, and further the flexibility of the entire manipulator was improved.

Those skilled in the art can readily making a variety of changes and modifications according to the description, drawings and claims provided by the present disclosure without departing from the thought and scope of the present disclosure defined by the claims. Any modification or equivalent change to the above embodiments according to the technical thought and substance of the present disclosure falls within the protection scope defined by the claims of the present disclosure.

What is claimed is:

1. A manipulator driven by modular joint time-sharing switching, comprising N identical sub segments, each of the N identical sub segments comprises: an external elbow tube assembly, an internal transmission assembly and an elbow tube drive unit;

the external elbow tube assembly comprises a fixed outer tube, a first outer tube connecting sleeve, a flexible outer tube, a driving nickel titanium wire, a supporting nickel titanium wire and a second outer tube connecting sleeve;

the fixed outer tube is a non-bendable sleeve structure, and is provided with sliding grooves symmetrically at both sides of a tube wall of the fixed outer tube; one end of the sliding grooves extends to an end face of the fixed outer tube; the first outer tube connecting sleeve is a sleeve structure, one end of the first outer tube connecting sleeve is provided with a shaft shoulder connected with the fixed outer tube, and the other end of the first outer tube connecting sleeve is connected with the flexible outer tube; the flexible outer tube is a unidirectional and bendable sleeve structure, both ends of the flexible outer tube are connected with the first outer tube connecting sleeve and a previous segment of the second outer tube connecting sleeve, respectively, through shaft shoulders at both ends of the flexible outer tube, the tube wall of the flexible outer tube is provided with through holes in a tube wall of the flexible outer tube evenly and circumferentially arranged; the through holes are divided into four groups at the upper, lower, left and right sides, respectively; the groups of through holes at the left and right sides are configured for mounting the supporting nickel titanium wire, and one of the groups of through holes at the upper and lower side is configured for mounting the driving nickel titanium wire; both ends of the supporting nickel titanium wire are clamped at the flexible outer tube by the first outer tube connecting sleeve and the previous segment of the second outer tube connecting sleeve, respectively; the supporting nickel titanium wire and the driving nickel titanium wire are both made of hyperelastic nickel titanium alloy wires; the second outer tube connecting sleeve is provided with a shaft shoulder in the second outer tube connecting sleeve, and both ends of the second outer tube connecting sleeve are connected with the fixed outer tube and a next segment of the flexible outer tube, respectively;

the internal transmission assembly comprises a transmission shaft core, an inner tube connecting sleeve and a flexible inner tube;

the transmission shaft core is a hollow shaft structure, both ends of the transmission shaft core are connected with the inner tube connecting sleeve through an internal spline, respectively; the inner tube connecting sleeve is a sleeve structure, one end of the inner tube connecting sleeve is connected with the transmission shaft core through an external spline, and the other end of the inner tube connecting sleeve is connected with the flexible inner tube; the flexible inner tube is a flexible hollow shaft structure, both ends of which are connected with the inner tube connecting sleeve through a shaft-milling plane structure;

the elbow tube drive unit comprises a threaded tube, a flange block, a threaded collar, an annular slide block and a temperature-controlled nickel titanium wire;

the threaded tube is a sleeve structure with a smooth inner wall, and is provided with a threaded structure at an outer side of the threaded tube, the threaded tube and the flange block are sequentially sleeved on the transmission shaft core; the threaded collar is sleeved outside the threaded tube to form thread transmission; an inner side of the annular slide block and the treaded collar are fitted with each other to fix the driving nickel titanium wire; an ear of the annular slide block is a bump structure slidable along an axial direction of the fixed outer tube in the sliding grooves of the fixed outer tube; one end of the driving nickel titanium wire is clamped at the flexible outer tube by the previous segment of the second outer tube connecting sleeve, and the other end of the driving nickel titanium wire is clamped between the threaded collar and the annular slide block; the driving nickel titanium wire is manipulated by the threaded collar and the annular slide block to achieve bending of the flexible outer tube; and the transmission shaft core is provided with a step capable of achieving a micro-displacement along an axial direction the transmission shaft core; the step is provided with two pinholes; the temperature-controlled nickel titanium wire is led out of a tube wall of the transmission shaft core and returns to the tube wall of the transmission shaft core after passing through the pinholes; the temperature-controlled nickel titanium wire is made of an energized-contractive nickel titanium alloy wire capable of driving the step on of transmission shaft core to achieve a micro-displacement along the axial direction of the transmission shaft core, so that the transmission shaft core contacts with the threaded tube and drives the threaded tube to rotate through friction.

2. The manipulator driven by modular joint time-sharing switching according to claim 1, wherein the flexible outer tube is a bendable but non-torsional nickel titanium alloy tube, with opposite spaced notches at both sides of the flexible outer tube to improve bending performance of the flexible outer tube.

3. The manipulator driven by modular joint time-sharing switching according to claim 1, wherein a plurality of wiring channels are arranged in the tube wall of the transmission shaft core for arranging electric wires and the temperature-controlled nickel titanium wire.

4. The manipulator driven by modular joint time-sharing switching according to claim 1, wherein the flexible inner tube is a bendable but non-torsional nickel titanium alloy tube, on both sides of which is provided with opposite spaced notches to improve bending performance of the flexible inner tube.

5. The manipulator driven by modular joint time-sharing switching according to claim 1, wherein the flange block is fixedly sleeved on the transmission shaft core, and the transmission shaft core is provided with two pinholes at a matching position with the flange block for leading the temperature-controlled nickel titanium wire out of the tube wall of the transmission shaft core; and the flange block and the transmission shaft core are connected with each other to fix both ends of the temperature-controlled nickel titanium wire.

\* \* \* \* \*